United States Patent [19]

Abels

[11] 4,193,405
[45] Mar. 18, 1980

[54] DETECTABLE MEDICAL AND SURGICAL IMPLEMENTS

[75] Inventor: Michael Abels, Miami, Fla.

[73] Assignee: Micro Tec Instrumentation Inc., Miami, Fla.

[21] Appl. No.: 914,615

[22] Filed: Jun. 9, 1978

Related U.S. Application Data

[62] Division of Ser. No. 712,883, Aug. 9, 1976, Pat. No. 4,114,601.

[51] Int. Cl.² ............................................. A61F 13/00
[52] U.S. Cl. .................................. 128/296; 128/303 R
[58] Field of Search .................. 128/2 P, 296, 303 R, 128/1 R, 156; 340/258 B

[56] References Cited

U.S. PATENT DOCUMENTS

| | | | |
|---|---|---|---|
| 3,097,649 | 7/1963 | Gray | 128/296 |
| 3,698,393 | 10/1972 | Stone | 128/296 |
| 3,834,390 | 9/1974 | Hirsch | 128/296 |
| 3,853,117 | 12/1974 | Murr | 128/2 P |
| 4,065,753 | 12/1977 | Paul, Jr. | 128/2 P |
| 4,114,601 | 9/1978 | Abels | 128/296 |

*Primary Examiner*—Robert W. Michell
*Assistant Examiner*—C. F. Rosenbaum

[57] ABSTRACT

Surgical implements, surgical instruments, surgical sponges, surgical implantable devices and indwelling therapeutic devices and materials may be detected within the human body or other area of interest by incorporating or adding a radiofrequency transponder. Non-linear mixing of two or more frequencies in a radiofrequency transponder is used. The transponder may be a small film deposition of Ferrite material exhibiting gyromagnetic resonance at selected frequencies or a solid state device.

2 Claims, 9 Drawing Figures

DETECTABLE MEDICAL AND SURGICAL IMPLEMENTS

This application is a division of Ser. No. 712,883, filed Aug. 9, 1976, and now U.S. Pat. No. 4,114,601.

BACKGROUND OF THE INVENTION

1. Field Of The Invention

The present invention pertains to a rapid economical fail-safe method to routinely detect retained surgical materials, i.e, surgical instruments, sponges, implantable devices, in dwelling therapeutic devices or materials.

2. Historical Background

Despite elaborate precautions, several times each year, patients who have undergone surgical operations have had surgical implements left in their bodies. These unfortunate incidents adversely affect the patient, the medical profession, involved doctors, hospitals, and involved insurance companies. Headlines announcing six and seven digit law suits and settlements are brought to the attention of the public with alarming frequency. There is a definite need for a system to routinely screen and detect retained surgical materials in the bodies of human patients while still under anesthesia and on the operating room table prior to the surgical wound closure.

3. Description Of The Prior Art

Currently, intraoperative visual inspection is the only routine method for detection of misplaced or retained surgical implements. X-ray examination is the only means of detection of such materials once the patient's body is closed. Surgical instruments being metal, are opaque to X-rays and easily seen in roentgengram. Sponges and ancillary materials are made radiopaque to X-rays by incorporation of radiopaque threads, e.g., barium impregnated latex.

While this method of surgical material detection is reliable, it suffers from numerous drawbacks and is not routinely used before closing the patient. To accomplish routine screening of all operative patients would be very costly in terms of equipment, operating room time, professional time, radiation safety enforcement and would entail additional X-radiation exposure to patients. To be done in the operating room prior to closing the patient's body would lengthen the operative procedure, inefficiently use the operating room and surgeon's professional time, and inevitably increase the cost of medical care.

The X-ray examination could be carried out in an area outside the operating room, e.g., the recovery room, but this becomes an "after-the-fact" detection, requiring the patient to be returned to the operating room, re-anesthetized, and re-opened for removal of the detected material with concurrent increased health and medical-legal risks entailed in a second procedure. Relocation of the procedure to an area outside the operating room would retain numerous financial and personnel drawbacks.

Yet another approach, not currently used, would be the use of radionucleides (isotopes) as tracers for detecting surgical implements with subsequent screening of the patients using scintillation counting equipment, survey meters or similar devices. Serious drawbacks to this concept are: accumulation of isotopically labeled material in the hospital would introduce burdensome regulation relative to isotopes; the increased background radioactivity of the operating room and hospital would cause increasing difficulty in the detection system itself and perhaps interfere with radioisotope assays in other areas of the hospital; the creation of a possible chronic radiation hazard to the operative personnel; the necessity for establishing and implementing radiation safety procedures. Lastly, the drawback relating to increased radiation exposure to patients and the possibility of long term radiation exposure to the patients if undetected radioactive materials were left in their bodies.

SUMMARY OF THE INVENTION

The present invention is summarized in the fact that non-linear mixing of two radiofrequency waves in a non-linear mixing medium, such as certain Ferrite materials exhibiting gyro-magnetic resonance or solid state devices such as diodes and field effect transistors, can produce the generation of higher order product frequencies as the result of non-liner mixing of the two search frequencies; and that, therefore, if this device is connected to small receiving and reradiating antenna, the entire device acts as a passive transponder. Several higher order product frequencies are obtained by the excitation of the transponder by the two fundamental search frequencies. By creating a system where two radiofrequency sources connect to antennas that direct radiofrequency energy in the direction of the transponder and a second radiofrequency antenna, connected to a product frequency receiver is used; means are provided to detect transponders. When the transponders are incorporated in different items, such as surgical implements, the detection of the transponder is equivalent to the detection of the implement.

It is the general object of this invention to create a radiofrequency detection system to be used as a surgical aid.

Further objects and advantages of the present invention will become apparent from the following description of the preferred embodiment in conjunction with the accompanying drawings.

DESCRIPTION OF THE PREFERRED EMBODIMENTS

Figure 1:
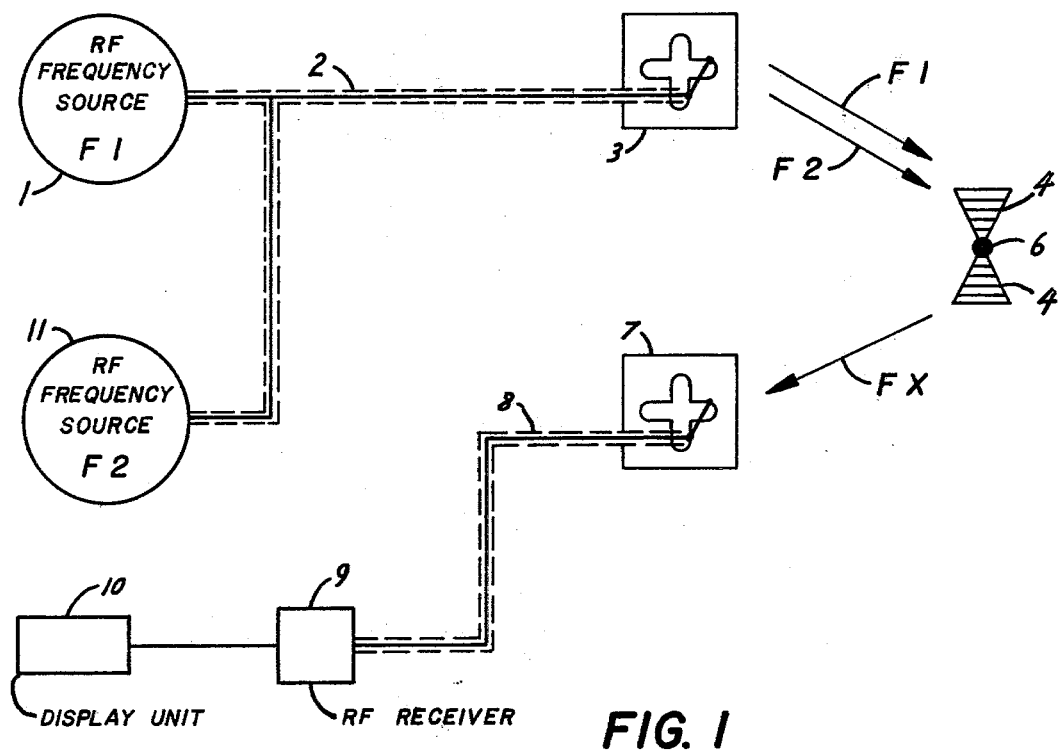
FIG. 1 is a block diagram of an embodiment of the surgical implement detector technique, according to the present invention.

The present invention is embodied in a radiofrequency transponder system, shown in block diagram form in FIG. 1. Although the system will operate at any frequency, the present state of the art in Ferrite technology and Ferrite conductor technology, coupled with the fact that a small transponder size is required, indicates that a suitable compromise is the use of a 4.5–5 Gigallertz band as the source of the two frequencies to be mixed in the transponder. A typical transponder size of 10–15 mm. by 3–4 mm. is indicated. Most of this area is occupied by metal foil elements, forming a simple elementary dipole or a more complex strip line type tuned circuit resonant at both the fundamental and product frequencies. Size of semiconductor junctions corresponds roughly to 0.5 mm., and Ferrite thin film depositions would have an area of 2 mm. square. The above dimensions and related frequencies are given simply as means of illustrating the preferred embodiments of the system, and are not considered limitations on this patent. As the state of the art progresses, it may be entirely feasible to use higher frequencies, and thereby smaller transponders in this application.

Item 1 is a micro-wave frequency source of frequency F1, connected to item 2, a coaxial cable, connecting in parallel to item 11, a second micro-wave source of frequency F2, and a circularly polarized "slot" type micro-wave antenna. For simplicity of description, all micro-wave sources and the "slot" antenna are shown connected in parallel, and the system does work well if impedances are close. In actual practice, a "hybrid" combiner is normally used to connect the two micro-wave sources to a single antenna, or conversely, generator F1 may be connected to a "slot" pair and generator F2 may be connected to a second "slot" pair. Item 3, the circularly polarized "slot" antenna consists of two cross slots, in a flat metallic surface. The micro-wave generators are "tapped" to the correct impedance point in the slots, approximately 1/10 wavelength for a 50 ohm system. Two slots are fed in phase, and the slots are crossed at 90° degrees to each other, causing the polarization vector to rotate. Circular polarization is preferable to linear in this application to minimize the effect of adverse transponder orientation. Both the antennas and transponders have sharp orientation nulls when using linear polarization (over 40 db of loss when cross-polarized in reference to each other). This is not the case when using circular polarization, the result of less than optimal orientation being a form of "elliptical" polarization varying only 3 db to a perfect circular polarity wave front.

Radiation from the antenna of item 3 is then the two micro-wave frequencies, F1 and F2. It should be understood that the above antenna description is used for illustration of the preferred embodiment only and that any suitable micro-wave antenna may be used. At higher "orientation" losses, linear antennas may also be used.

Radiation from item 3 is directed on items 4 and 6. Items 4 and 6 are in combination a radiofrequency transponder, capable of producing higher order product frequencies, collectively indicated as Fx. Item 4 is a metallic foil antenna, directing radiofrequency energy to item 6, a non-linear mixer, that may be either of the resonant Ferrite type or of the semiconductor type. Besides intercepting radiofrequency waves at the fundamental frequencies, item 4 also acts as a radiating antenna for all frequencies, the frequency of interest in this particular application being one of the higher order product frequencies (Fx), different from the two search frequencies (F1 and F2).

As an example, assume the two fundamental frequencies, close enough to each other, to have a common tuned circuit, i.e., 4.4 and 4.6 GigaHertz. Numerous higher order product frequencies are produced, and a transponder roughly resonant to the fundamental as a first order resonance, is also resonant to several of these higher order product frequencies.

Transponder elements are later described in more detail. The transponder radiates product frequency Fx towards a receiving antenna, item 7 in FIG. 1. The receiving antenna connects through item 8, a coaxial cable to item 9, a micro-wave receiver tuned to the product frequency of interest.

The receiver, item 9, must have certain characteristics for optimum performance. It must be well filtered at the input, to reject both fundamentals and prevent non-linear mixing at the receiver front end from generating the higher order product frequencies of interest. In the frequency example given before, filtering takes place over more than one octave range, 4.5 GigaHertz to 9 GigaHertz, and is not complex. As compared to second harmonic generation and reception, which requires extreme filtering at both the frequency source and the receiver, higher order product frequency detection offers the advantage of operating at a frequency that is not normally present at the output of either micro-wave source, regardless of filtering.

The receiver is followed by item 10, a display unit showing in visual and/or audible terms that a transponder is present in an area scanned using the system. In addition, the display unit indicates the presence of extraneous interference that might lead to false positive or false negative results in the detection system. The display indicator unit may have the following displays, a green light indicating no transponders are present in the field of search, a red light indicating the presence of transponders in the field of search, and a yellow light indicating the presence of extraneous micro-wave interference in the operational environment of the system. In addition, various audible tones, bells and buzzers, may be used. Though it is not necessarily limited to these, the above example being used only for illustration.

Figure 2:
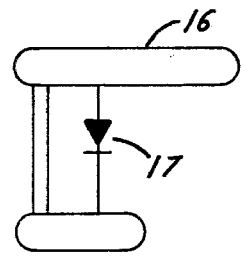
FIG. 2 is a detail of transponder construction, both for Ferrite devices and semiconductor devices.
Figure 2:
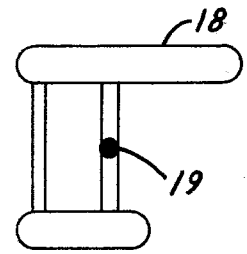

FIG. 2 shows typical transponder configurations, though the present embodiment is not necessarily limited to those configurations shown, given here as an illustration. Item 12 is a foil antenna, made of any suitable metallic foil or conductive (electrically) material. Typically, it might be 5 mm. long for each of the two elements forming the elementary dipole.

Item 13, a thin film Ferrite disc placed between both dipole elements acts as the higher order product frequency converter, generating product frequencies by the interaction of the two radiowaves, closely spaced in frequency, with a Ferrite material that has a close equivalent gyro-magnetic or spin resonance, frequency. The effect of the combined radiowaves is to accelerate or slow spin phenomena, giving rise to non-linear mixing, by the action of two closely related spins in the same Ferrite, creating higher order perturbations of electronic or molecular spin, and therefore creating higher order products.

Suitable Ferrite materials are listed below, although this patent is not necessarily limited to these, but rather applies to the phenomena of spin frequency generation using Ferrites as a whole, including some new materials or "Garnets" that may be created in the future during the life of this patent.

---

MATERIALS, FERRITES,
COMPOUNDS BASED ON THE FORMULAS:

| | |
|---|---|
| $ZnO$, $MnO$, $NiO$, $Fe_2O_3$, | (soft powdered, sintered.) |
| $Ba\, Fe_{12}O_{19}$ | (permanent) |

-continued

MATERIALS, FERRITES, COMPOUNDS BASED ON THE FORMULAS:

particularly those used as resonant elements, i.e.-

| | |
|---|---|
| $MnO\text{-}xAl_2O_3(1\text{-}x)\ Fe_2O_3+$ | (2,000 to 5,000 Mhz) |
| $NiFe_2O_4$ 80% $CuFe_2O_4$ 20% | (5,000 Mhz) |
| $NiFe_2O_4$ 80% $ZnFe_2O_4$ 20% | (8,000 Mhz) |

For reference, see ITT Ref. Data Handbook, 4.39, Microwave resonant Ferrites.

Or any Ferrite garnet, ceramic ferro electric compound, or combinations of Ferrites ions in crystals, provided that they exhibit gyro-magnetic or spin resonance at frequencies close to the selected frequency of operation.

Items 14 and 15 illustrate a transponder made with a semiconductor device, such as a diode, capable of operating in the frequency range of interest as a higher order product frequency generator. Item 14 is the antenna or radiating element, item 15 is the semiconductor.

Items 18 and 19 show a Ferrite transponder element, where the transponder is a strip line circuit, tuned to both the fundamental and higher order product frequency products, item 18 is the antenna and item 19 is the Ferrite disc. Items 16 and 17 show a similar transponder (tuned strip line circuit type) this time with a semiconductor as the mixer, item 16 is the antenna; item 17 is the semiconductor.

Though the tuned strip line circuit transponders exhibit a higher Q and better efficiency as radiators, this is not so when the transponder is surrounded by tissue or held in close proximity to flesh. The transponder detunes, i.e., when held in a closed fist, and its efficiency reduces to almost that of an elementary dipole. In most cases, it is not necessary that the transponder be an exact electrical quarter wavelength (normal criteria for micro-wave antenna), but it may be less, 1/8 wave or less of the fundamental. Its efficiency decreases the smaller the elements being used. Because the distance over which the test is made is only in the order of two feet, the transmitted power may be high (within RF radiation safety limits), and a relatively inefficient transponder may be used.

Tests have indicated that with 0.5 watts of transmitted power from the micro-wave sources, a system would have a dynamic range in excess of 90 db, and use sensitive receivers with a sensitivity of $-100$ db minimum, for reliable operation in close proximity to human or animal tissue.

In order to prevent damage and aid in the ease of incorporation, the transponders may be encapsulated in teflon or more rigid plastic or may be impregnated into or form the core of a teflon thread or similar material.

Figure 3:
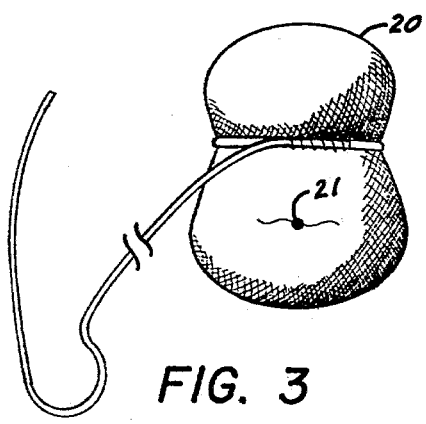
FIGS. 3, 4, and 5 are details of typical transponders attached to various surgical sponges.
Figure 4:
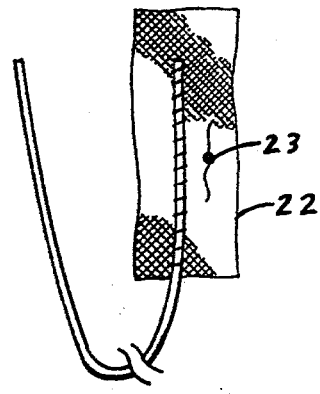
Figure 6:
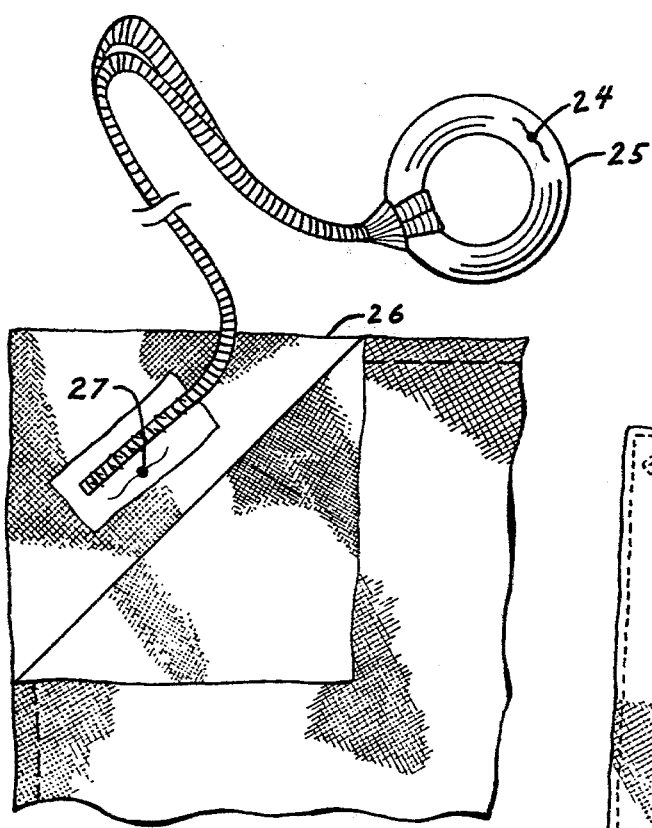
FIG. 6 is a detail of FIG. 5.
Figure 5:
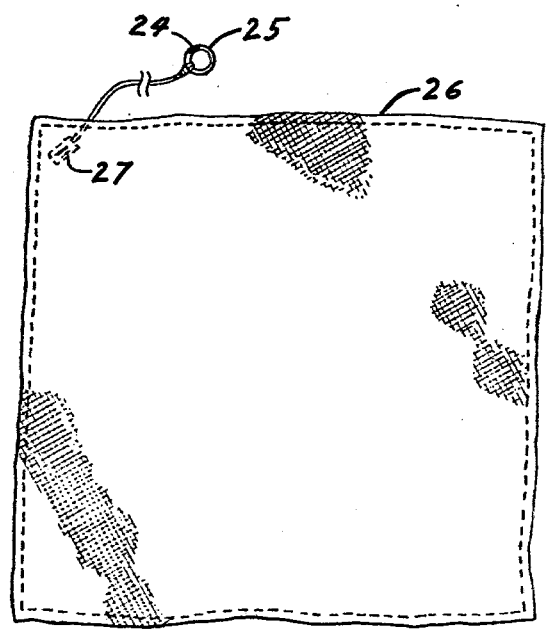

FIGS. 3, 4 and 5 show typical applications of transponders to surgical sponges. Items 20, 22 and 26 are transponder implanted surgical sponges, items 21, 23 and 27 being the incorporated transponders. Item 26 is a lap pad with attached plastic ring (item 25). Item 24 is a transponder incorporated in item 25, the ring. FIG. 6 is a detail of FIG. 5 showing items 24, 25 and 27 in more detail.

Figure 7:
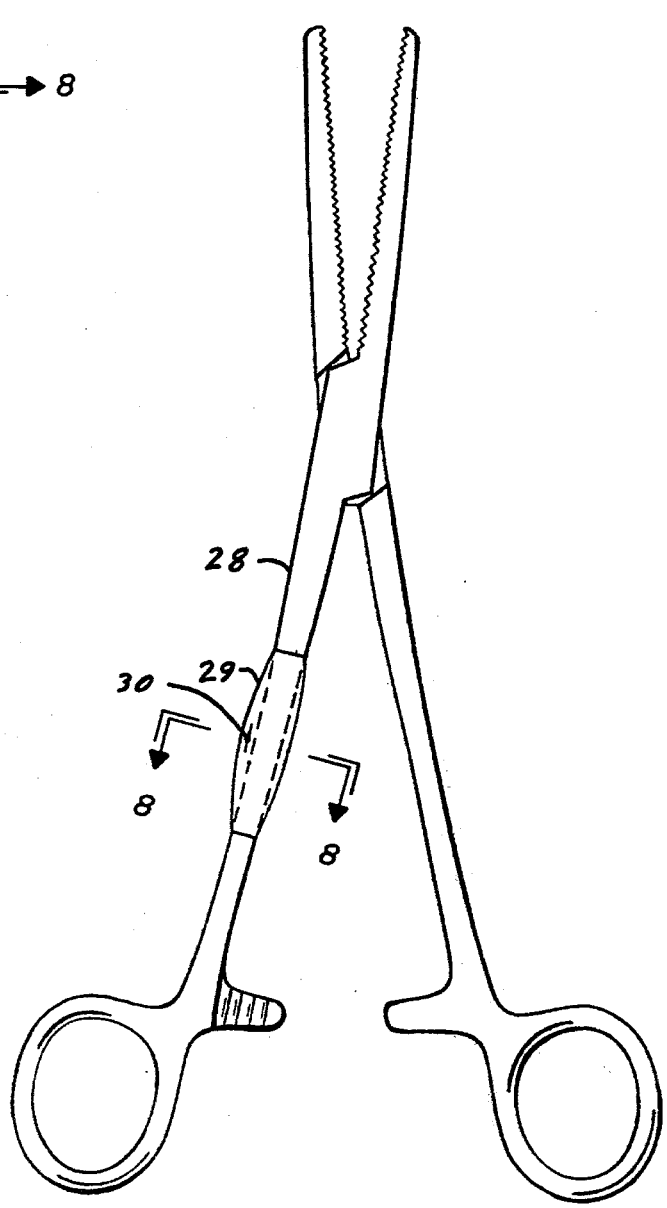
FIG. 7 is a detail of a means to attach transponders to surgical instruments, that is flexible and permits attachment of transponders to many types of instruments and implements.

FIG. 7 shows a method of adding a transponder to a surgical instrument. Item 28 is a typical surgical instrument, a hemostat, item 29 is a sleeve of teflon or other suitable material incorporating a transponder, item 30, properly spaced from the metal instrument.

Figure 8:
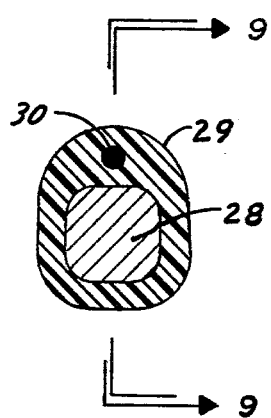
FIG. 8 is a cross section through FIG. 7 along line 8—8.

FIG. 8 is a cross section through FIG. 7 along line 8—8 showing item 29, the encapsulation sleeve, item 30, the transponder and part of item 28, the instrument.

Figure 9:
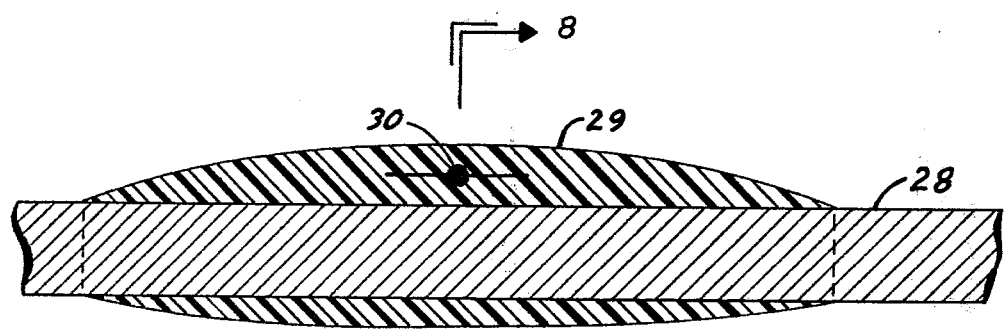
FIG. 9 is a longitudinal section through FIG. 8 along line 9—9.

FIG. 9 is a longitudinal section through FIG. 8 along line 9—9 showing item 29, the encapsulation sleeve, item 30, the transponder,, and part of the instrument, item 28.

The above figures are given simply as a means of illustrating the preferred embodiments of the system, and are not considered limitations on this patent.

METHOD OF OPERATION

During the course of a surgical procedure, all instruments, sponges, implements, etc., used shall have a transponder incorporated. At the termination of the operative procedure, after the operating room staff has performed the sponge and instrument counts, but prior to the surgical wound closure, the surgeon would screen the patient's body while on the operating table for the presence of any retained surgical implements incorporating transponders, using a lightweight, hand held, transceiver antenna unit. After a negative screen, the wound would be closed and the patient sent to the recovery room with confidence that no surgical materials were inadvertently left within the patient's body.

Alternately, devices may be deemed to be present, as desired, by use of this system.

The application of the system may also be extended for similar use in animals or other areas of interest.

I claim:

1. A surgical sponge detectable within the human body comprising of surgical absorbant material incorporating a transponder capable of non-linear mixing of two or more radiofrequency signals impinging thereon, to thereby generate and reradiate a higher order product frequency; directing two or more radiofrequency signals towards the portion of the human body to be investigated; placing receiving means in the vicinity of said investigated portion to detect and visually or audibly indicate the presence of any reradiated higher order product frequency signals emanating from the investigated area; the existence of said reradiated signals indicating that said surgical sponge is within the human body.

2. A surgical instrument comprising instrument means to perform surgical manipulation, detectable within the human body incorporating a transponder capable of non-linear mixing of two or more radiofrequency signals impinging thereon to thereby generate and reradiate a higher product frequency; directing two or more radiofrequency signals towards the portion of the human body to be investigated; placing receiving means in the vicinity of said investigated portion to detect and visually or audibly indicate the presence of any reradiated higher order product frequency signals emanating from the investigated area, the existence of said reradiated signals indicating that said surgical instrument is within the human body.

* * * * *